United States Patent [19]

Kawam

[11] Patent Number: 5,094,248
[45] Date of Patent: Mar. 10, 1992

[54] DEVICE AND METHOD FOR SIMPLE VISUAL MEASUREMENT OF THE AMOUNT OF SEBUM PRESENT ON HUMAN SKIN

[75] Inventor: Antoine Kawam, Washington, D.C.

[73] Assignee: The Gillette Company, Boston, Mass.

[21] Appl. No.: 726,728

[22] Filed: Jul. 1, 1991

Related U.S. Application Data

[63] Continuation of Ser. No. 60,261, Jun. 10, 1987, abandoned.

[51] Int. Cl.⁵ ................................................ A61B 5/00
[52] U.S. Cl. ..................................... 128/759; 128/760
[58] Field of Search ............................... 128/759, 760

[56] References Cited

U.S. PATENT DOCUMENTS

| | | | |
|---|---|---|---|
| 3,425,412 | 2/1969 | Pope | 128/154 |
| 3,542,634 | 11/1970 | Such et al. | 128/156 |
| 4,224,950 | 9/1980 | Bore et al. | 128/759 |
| 4,313,393 | 2/1982 | Barbuscio et al. | 116/200 |
| 4,480,921 | 11/1984 | Leveque et al. | 356/434 |
| 4,483,619 | 11/1984 | Leveque et al. | 356/434 |
| 4,494,869 | 1/1985 | Neumann | 356/36 |
| 4,532,937 | 8/1985 | Miller | 128/759 |

FOREIGN PATENT DOCUMENTS

| | | |
|---|---|---|
| 1117787 | 2/1982 | Canada . |
| 2368708 | 5/1978 | France . |
| 2404845 | 4/1979 | France . |
| 2043886 | 5/1983 | United Kingdom . |

Primary Examiner—Randy C. Shay
Attorney, Agent, or Firm—Burns, Doane, Swecker & Mathis

[57] ABSTRACT

A hydrophilic sebum collecting device including a strip of hydrophilic open celled microporous polymeric film. Also provided is a method for the quantification of sebum in a patch of skin by applying a hydrophilic open celled microporous polymeric film to the patch of skin such that the film is retained in sebum collecting contact therewith. The film is retained in sebum collecting contact for a period of about 5 to 30 seconds and at a predetermined pressure. The film is eventually removed from the patch of skin and placed over a scaled background such that the amount of sebum collected by the film can be determined by comparison with the scaled background.

16 Claims, 1 Drawing Sheet

DEVICE AND METHOD FOR SIMPLE VISUAL MEASUREMENT OF THE AMOUNT OF SEBUM PRESENT ON HUMAN SKIN

This application is a continuation of application Ser. No. 07/060,261, filed June 10, 1987, now abandoned.

BACKGROUND OF THE INVENTION

The present invention relates to a device and method for collecting and quantifying sebum content on a patch of skin, to determine the natural presence thereof.

Epidermal or skin-surface fat, also known as sebum, cannot be said to consist of any one substance. It mainly consists of the secretions of the sebaceous glands, the fat of the keratinous layer and remnants of perspiration. Sebum forms a thin film that coats the skin and is generally formed at both the sebaceous glands and in the keratinous layer before exposure to secondary influences after secretion. Schaaf, F: Probleme dermatologischer Grundlagenforschung, Dr. Alfred Huthig-Veriag. Heidelberg, 1969. (Basic Research Problems in Dermatology.)

Sebum film has a number of important functions in the skin's protective mechanisms. For example, it affects the skin's permeability and absorptivity of water. It protects against environmental threats, limits evaporation thus preventing excessive drying, and affects the penetration of pharmaceutical preparations and other active or non-active substances. Deprived of this lipid containing film, the epidermis would lose its moisture at an accelerated rate resulting in dry, chapped, scaly skin conditions and the loss of suppleness. See Schneider, W., Die Bendeutung, Experimenteller Untersuchungen des Lipid-Wasser-Gehaltes an der Haut fur die externe Therapie, Derm. WSCHR., 147, 1963, pp. 1-7. Concerning the significance for external treatment of experimental work on the lipid and water content of skin.

Hence, the measurement of the natural presence of sebum on human skin, and particularly facial skin, is a problem of current interest among dermatologists, pharmaceutical manufacturers and cosmetics manufacturers. The cosmetic industry is particularly interested in such measurements since the quantitative assessment of skin oiliness enables the beautician or cosmetics sales clerk to recommend an optimal assortment of cosmetics.

In cosmetics, pharmaceuticals, and dermatology, different types of apparatus exist for measuring the amount of sebum secreted by the skin of a living subject. Most of these apparatus are based on the fact that when sebum is deposited on a translucent element, such as a frosted glass or plastic plate or strip, the element becomes increasingly transparent (the greater the amount of sebum applied, the greater the transparency produced). One method of measurement consists of subjecting the sebum covered translucent element to a luminous flux and measuring the amount of light which passes through the translucent element by the use of a photoelectric receiver. Schafer, H. und Kuhn-Bussius H., Methods regarding quantitative Determining of Fat Secretion. Archives of the Clinical-Experimental Dermatology, 238. 429-435, 1970.

The quantitation of sebum secretion in human skin has been the basis for most of the photometric apparatus and methods used to date. Light transmission through opalescent (frosted or ground) glass is increased when the rough surface is fatted with sebum. There is a constant relation between the change of the transmission and the weight of fat upon the frosted glass elements being pressed to the forehead. By comparing the measurements of known amounts of petrolatum distributed on the forehead, quantitative measurements of the casual level of surface fat related to the function of the sebaceous gland secretion has been obtained. This observation has prompted a number of patents describing apparatus of various types that are suitable for clinical measurements of sebum. These patents include: French Patent Nos. 2,368,708; 2,404,845; United Kingdom Patent Nos 1,590,598, 2,022,818 and 2,043,886; and U.S. Pat. Nos. 4,480,921 and 4,483,619.

U.S. Pat. 4,494,869 is based on a modification of the principles stated above. A smooth, optically clear lens is contacted with the skin to collect droplets of sebum on its sampling surface. Then, light emitted from an optical source is passed through the sampling surface and focused onto an optical detector. The output signal of the detector is displayed to give an indication of the degree of oiliness or sebum content of the skin.

A technique of Strauss and Pochi uses parts of ether-extracted cigarette paper to collect sebum as the function of time. The collected sebum is determined gravimetrically. Strauss, J. S., Pochi, P. E.: The Quantitative Gravimetric Determination of Sebum Production. J. Invest. Dermatol. 36:293-298 (1961).

A technique of Downing, Stranium, and Strauss uses a bentonite absorbent to collect sebum that is then assayed by thin layer chromatography. Downing, D. T., Stramen, A. M., Stauss, J. S., The Effect of Accumulated Lipids on Measurements of Sebum Secretion. J. Invest. Dermatol. 79:226-228 (1982).

However, none of the above-cited methods lends itself to use by a cosmetician or a salesperson, a doctor, or a pharamacist outside of a clinical laboratory.

The "Sebumeter", described in German Offenlegungsschift 2,353,224, has been developed to facilitate the sebum sampling operations. See also, Schrader, K: A New Procedure for the Determination of Skin-Surface Fat. Dracogo Report, 8/74, pp. 171-174. This apparatus requires very little training on the part of the operator and consists of two separate components; namely a sampling device, and a measuring device which is equipped with a photoelectric receiver and a source of illumination. The sampling device comprises a casing, from which projects a sample-holder on which the translucent element (plastic tape) is arranged. The sample-holder is connected to the casing by a calibrated spring to enable the sample-holder to be applied, under an approximately constant pressure, to the patch of skin to be studied. After having sampled the sebum, the sample holder is carried into the photoelectric measuring device of the apparatus in order to evaluate the amount of sebum secreted. Although the "Sebumeter" represents an improvement over the other above-cited references, it still has numerous problems and limitations. For example, the contact time at a rather high pressure is 30 seconds. This can become somewhat tedious when dozens of tests, including the preparation and repreparation of the apparatus, are conducted per hour. Further, the apparatus is costly and requires the continual purchase of a cassette containing the plastic film sampling device which is also fairly costly, particularly when the usage of this machine at a cosmetic counter could well exceed 100 tests in a few hours.

There have been some attempts along the lines of a litmus or pH paper type device, namely U.S. Pat. No.

4,313,393, which describes an indicator device for determining the dry, normal, and oily characteristics of human hair and scalp. The apparatus comprises an oil absorbent indicating material, treated with an oil soluble dye and surrounded by an oil permeable membrane. See also U.S. Pat. No. 4,313,393, 2/1983, Barbuscio et al. However, investigation of the disclosed process and apparatus has indicated several problems with the technique including : (1) the indicator was designed for hair and scalp and if used on face and forehead, the oil soluble dye could likely come in contact with the skin, and cause irritation, and the dye could also transfer to and discolor the skin; (2) the level of oiliness is estimated as a function of the depth of the color developed. Frequently it becomes difficult and confusing for the users or consumers to analyze their skin type such as normal, oily, and dry conditions, by this type of subjective analysis. Further, a color-based analysis is particularly impractical for those who are color blind; and (3) the method of affixing the laminated device to the skin is tedious and unattractive.

U.S. Pat. No. 4,532,937 (European Patent No. 129598) represents an improvement over the indicator device described above. It describes an accurate and simple device for collecting sebum as it is secreted. It is comprised of an open celled, microporous, hydrophobic polymeric film, coated with a special pressure-sensitive adhesive that does not migrate into the micropores of the film. The film is affixed to the skin by means of the adhesive, thus making it similar to an adhesive bandage. As sebum is secreted from the skin, it can flow through the adhesive into the pores of the film. Originally the film is opaque-to-light or opalescent in appearance. It will become substantially translucent when the pores are filled with sebum. The level of transparency is proportional to the quantity of oil absorbed from the skin contact site which is controlled by the amount of sebum present on the skin. A commercial indicator device based on this patent is currently marketed under the trade name SEBUTAPE (trademark of Cuderm Corporation, Dallas, Tex.).

To facilitate the reading of the level of sebum collected (intensity of translucency), several convenient reference patterns of various intensities are provided. The user removes the tested tape and places it on a black background that is provided. The pores of the tape that are filled with sebum will become more visible as multiple black color dots patterns. Comparison with a precalibrated reference pattern for skin type allows definition of the type of skin (i.e. the amount of sebum generated). The directions accompanying this device require facial cleansing to establish a reference point which is followed by taping over six recommended facial sites (right and left forehead and cheek, as well as nose and chin). The six film strips with adhesive backings have to remain on the test sites for at least one hour. Example 1 of the U.S. Pat. No. 4,532,937 cites 3 hours of application. This patent claims the combination of using the unique feature of the adhesive on a microporous, hydrophobic polymeric film which is made by Celanese and marketed as Celgard ® grade 2400.

Despite its simplicity and advantages over other methods, this device has considerable drawbacks which are preventing general acceptance and use by consumers, namely: (1) it is extremely inconvenient and tedious for users to function with several adhesive-backed plastic strips stuck on several facial test sites for up to three hours; (2) no matter how benign the adhesive is, users with a sensitive skin would suffer inconvenience and temporary irritation from such a lengthy exposure; and (3) the overall cost is still relatively quite high.

To meet the needs of the large number of cosmetics users and dermatology patients, and at the same time, facilitate the job of beauticians, sales clerks, doctors, and pharmacists, an indicator along the lines of litmus or pH paper is badly needed. The device should combine simplicity, accuracy, ease of use, safety, and low cost. To date, such criteria have not been met, and as a result no indicator type device is enjoying wide acceptance.

It is obvious that if the problems associated with such a device could be eliminated, the resulting indicator device would meet the ideal product criteria. Furthermore, it would lend itself to dissemination through inserts in magazine ads, permitting the user to perform the necessary skin oiliness measurement and then order the recommended products for a specific skin condition.

OBJECTS AND SUMMARY OF THE INVENTION

It is therefore an object of the present invention to provide a simple, safe, non-irritating, accurate device and method of use eminently suited to put into the hands of consumers directly with simple-to-follow instructions and no supervision.

It is another object of the present invention to provide a hydrophilic sebum collecting device.

It is also an object of the present invention to provide a method for the quantification of sebum in a patch of skin.

In accordance with one aspect of the present invention, there is provided a hydrophilic sebum collecting device. The device includes a strip of hydrophilic open celled microporous polymeric film.

In accordance with another aspect of the present invention, there is provided a method for the quantification of sebum in a patch of skin. In so doing a hydrophilic open celled microporous polymeric film is applied to the patch of skin such that the film is retained in sebum collecting contact therewith. The film is retained in sebum collecting contact for a period of about 5 to 30 seconds and at a predetermined pressure. The film is eventually removed from the patch of skin and placed over a scaled background such that the amount of sebum collected by the film can be determined by comparison with the scaled background.

DETAILED DESCRIPTION OF THE PREFERRED EMBODIMENTS

It was found that by use of a hydrophilic open celled microporous polymeric film, the amount of time that the film must be maintained in sebum collecting contact with a patch of skin can be reduced to seconds. By "sebum collecting contact" is meant a contacting side of the film is placed into intimate contact with a patch of skin such that sebum can pass through the pores of the film and be collected therein. The film can be either initially hydrophilic or can be made hydrophilic by treating a hydrophobic open celled polymeric film, such as the films used in U.S. Pat. No. 4,532,937, which is hereinafter incorporated by reference, with surfactants to render it hydrophilic.

Because of the decrease in time required to collect sebum, the use of adhesive for affixing and retaining can be eliminated and replaced by the simple use of fingers to hold the film in place. However, adhesive can be used to provide a uniform method of application and retention of the film, at a substantially uniform pressure without risk of irritation due to over exposure to the adhesive.

Figure 2:
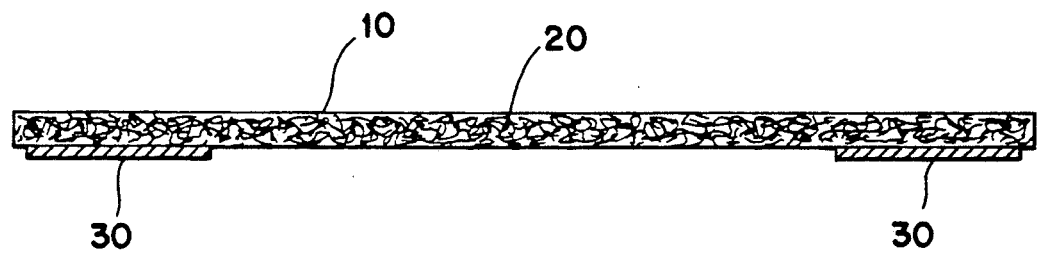
FIG. 2 is a side view of a particular embodiment of the present invention.

As illustrated in FIG. 2, the device 10 may comprise a hydrophilic film 20 having an adhesive 30 distributed at opposing ends of a contacting side of the film to create an intermediate zone which is substantially free of the adhesive.

While many polymeric materials are in principle suitable for the films of this invention, commercial availability and economics dictate that the preferred film material be polypropylene. The type of polymer, and the polarity of the film are not the only factor affecting the rate of pore filling. Film thickness is another property that affects the rate at which the pores are filled to produce the transparency change. A thickness range of 0.01 mm to 0.05 mm is acceptable with 0.025 mm (1 mil) being preferred. A porosity range of 30–60% is suited for the invention with 45–50% being preferred. An effective pore size range of 0.01 to 0.05 is acceptable, while 0.04 to 0.05 is preferred.

The pores of the basic unmodified hydrophobic polymer propylene film have the inherent characteristics of polypropylene, namely a surface tension of 35 dynes/cm. The surfactant treated film covered by this invention has a surface tension greater than 50 dynes/cm and still more preferably greater than 65 dynes/cm.

The present invention provides numerous advantages over prior art sebum collecting devices and methods and particularly over those disclosed in U.S. Pat. No. 4,532,937. For example, since the amount of time required for sebum collection is reduced to seconds, the need for complex or irritating application/retention devices is obfuscated. Because the device and method are so simple, the ultimate consumer or patient could conduct these measurements easily at home at greatly reduced cost and with no pain or inconvenience. Further, the present invention lends itself to a wide dissemination through inserts in magazine ads and other such medium.

While the selection of the sebum collecting material is important, other factors must be taken into consideration when designing a background. The background is a visual indication device which is scaled to reveal the amount of sebum in the skin when compared to the film.

In constructing a background, it is necessary to select a method of classification for identification of sebum content upon comparison. This method of classification is also known as a scale or calibration. SEBUTAPE patches for instance, provide reference patterns for 6 levels of skin oiliness designated as 0-1-2-3-4-5. The Sebumeter suggests a scale of Dry; Dry/Normal;Normal;Normal/Oily;Oily. Commonly, one finds studies describing essentially three types of skin: Dry; Normal; Oily.

Any method of classification falls within the scope of this invention. A 4-category scale of: Dry, Normal/Dry, Normal/Oily or Oily has been selected and the calibration below is based accordingly.

To construct a background with a comparison calibration, individuals are selected whose skin has been well characterized, by themselves and by a beautician, to fall within each of above four categories. Sebumeter measurements are performed on these subjects for comparison and reference purposes. The Sebumeter has the advantage of rating on a numerical scale:

| Skin Condition | Sebumeter Reading |
| --- | --- |
| Dry | 0–100 |
| Normal/Dry | 100–175 |
| Normal/Oily | 175–250 |
| Oily | >250 |

Since the secretion of sebum is a continuous process defined in terms of weight of sebum produced per unit time (hours) per unit skin area (generally $cm^2$), it is necessary to select a reference point for any measurement and rating of skin oiliness. This reference point is established by performing a thorough general cleansing. Sebum is then allowed to accumulate for a specific period of time. For the following, 3 hours has been selected. Hence, the following measurements compare the amount of sebum generated during a 3-hour period. It should be noted that the same approach could well be taken for other periods of time, but would require a recalibration. A strip of "Celgard" ® K-381, Celanese's brand of microporous polypropylene film, is used in all the tests.

Celgard ® K-381 is a specialty grade made by modifying a standard Celgard ® 2500 base film with a medical grade non-ionic surfactant to render it hydrophilic. Its specifications are:

| | | | |
| --- | --- | --- | --- |
| Thickness | 0.025 mm (1 mil) | | |
| Density | 0.49 g/cc | ASTM | D-1622 |
| Porosity | 45% | ASTM | D-2873 |
| Pore Density | $7 \times 10^9$ pores/$cm^2$ | | T.E.M. |
| Nominal Pore Dimensions | $0.04 \times 0.40$ micron | | T.E.M. |
| Effective Pore Size | 0.04 micron | | T.E.M. |
| Critical Surface Tension | 70 dynes/cm | ASTM | D-257B |
| Flow Rate of Air at 76 cmttg | 300 $cm^3cm^2$/min | Spec. | # D-3005 |

Figure 1:
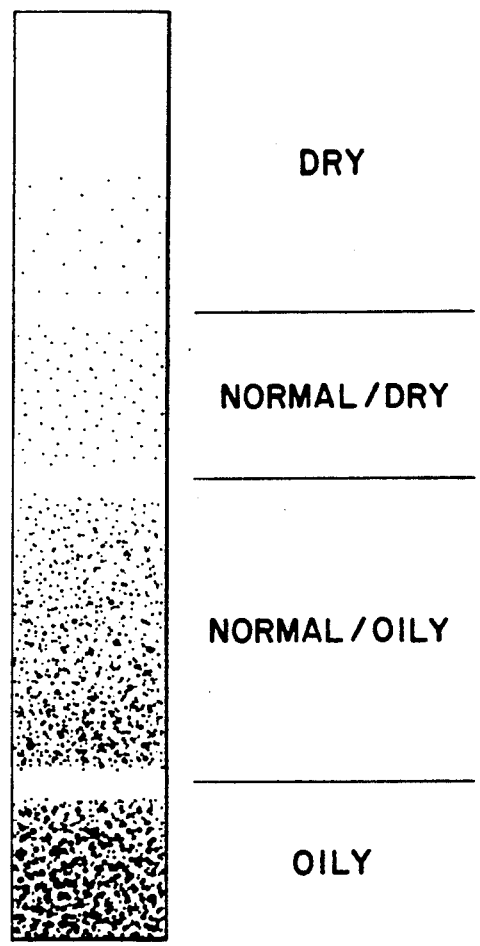
FIG. 1 illustrates a representative set of reference standards for use in the practice of the method of the present invention.

The following technique can be used to calibrate a test strip. A group of panelists is assembled; these possess by their own judgment as well as by the judgment of an experienced cosmetician the four types of skin cited earlier. After cleansing their faces, they perform their normal activities without the application of any skin treatment for three hours. The film, which may be applied, and retained in sebum collecting contact by hand, is applied to the patch of skin to be tested. Measurements are then made on the basis of a 3-hour sebum collection period. A large number of tests are performed by manually holding and retaining strips of Celgard ®K-381 to the patch of skin for periods of between about 5 to 30 seconds at a predetermined pressure of light, medium and heavy finger pressure. The strips are removed and placed over a background as shown in FIG. 1 to show various concentrations of black dots. Normally the Celgard ® is pearlescent and with an opacity of 70% (AS D-2244), and thus it passes a rather limited amount of light. As it collects sebum, it develops clarity proportional to the amount of sebum collected. Because of its unique microcellular structure, this clarity appears in the form of dots and not as a continuous coating, thus making it easier to assess visually.

The data collected can be analyzed and compared to define the most convenient condition of time/pressure to provide 4 distinct patterns of dot concentration which can be set as reference standards and supplied to the user for assessment of one's own skin oiliness condition.

In order to further illustrate the present invention and the advantages thereof, the following specific examples are given, it being understood that these examples are intended only to be illustrative without serving as a limitation on the scope of the present invention.

EXAMPLE 1

A 1 and ½×2 and ½ cm strip of Celgard® K-381 microporous polypropylene film wrapped or covered to protect it from contamination is supplied with a black background surface for convenience in conjunction with four reference patterns as illustrated by FIG. 1. Each pattern is a white background with a certain concentration of black dots corresponding to the average composite concentration obtained from the previously described clinical study with the panelists. The lowest concentration corresponds to the "Dry Skin", the heaviest is the "Oily", with "Normal/Dry" and "Normal/Oily" being the two intermediate levels.

The user is instructed to handle the strip from the edges with clean fingers to avoid transferring any oily substance to its surface. The strip is applied over the site of the face being measured with moderate pressure for 20 seconds then removed. To avoid contamination from fingers while holding it over the skin, the wrapping into which the strip is inserted could provide a cover to protect the strip from direct finger contact.

The test strip is then removed completely from its wrapping while handling it from the edges, then superimposed over the dark background developing surface provided.ABstracts will appear. It can also be advantageous to provide each test strip with its own black wrapping for immediate reading after completion of the test; thus the wrapping and the strip can remain attached during testing with the wrapping serving to shield the Celgard® K-381 strip from finger contact during the test.) Visual comparison with the 4 reference dot patterns will establish which level constitutes the closest match. A rating is thus obtained very rapidly, with no instrumentation and in a manner that lends itself to distribution through the mail or magazine insert advertisements or handouts for self use.

EXAMPLE 2

Another method to practice the present invention that would be more suitable for use by beauticians, estheticians, salespeople, etc., involves a very slight modification to improve the overall process. If the strip were to be used by a person from the trade to sell a product to a consumer, the process described earlier can become tedious since hundreds of tests are performed in a short time. The time/pressure relationship is an important combination of variables in this test. Time can be accurately measured, finger pressure cannot. If a 5-10 second contact time is desired, heavier and inconvenient pressure needs to be applied. Twenty seconds has been selected as requiring mild to moderate pressure.

A very simple applicator has been developed to hold the strip in place over the skin with uniform, mild, premeasured pressure for the desired amount of time. Such applicator comprises a flat surface of the same size as the strip with a telescoping handle made of 2 separate parts (piston/cylinder) with a compression spring located inside the cylinder over which rests the piston. The piston is calibrated along its length to show when pressures of 100-200-300-400-500 grams are reached as the piston is pushed against the spring inside the cylinder. This is a research tool to be used in the studies needed to develop the best combination of shortest time and most comfortable pressure.

When sebum has been accumulating for a period of 3 hours, the application of 300 g weight of pressure for 15-20 seconds becomes quite convenient.

Hence an applicator built to reach its ultimate compression at a 300g weight force can be constructed and distributed to the sales personnel and beauticians to assist them in selling cosmetics designed for each skin type. Twenty seconds of contact time can provide enough data to show four distinct patterns. The calibration and comparison are performed as previously described.

The principles, preferred embodiments and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention.

What is claimed is:

1. A sebum collecting device, comprising (1) a strip of hydrophilic open celled microporous polymeric film of size and shape adapted for contact with skin and the collection of sebum and (2) an application/retaining means for retaining said film in sebum collecting contact with a patch of skin.

2. The device of claim 1, wherein said film thickness is from about 0.01 to about 0.05 mm.

3. The device of claim 2, wherein said film has a film thickness of about 0.025 mm.

4. The device of claim 1, wherein said film has a porosity of about 30 to about 60 percent.

5. The device of claim 4, wherein said film has a porosity of about 45 to about 50 percent.

6. The device of claim 1, wherein said film has a surface tension of greater than 50 dynes/cm.

7. The device of claim 6, wherein said film has a surface tension of greater than 60 dynes/cm.

8. The device of claim 7, wherein said film has an opacity of from about 60 to about 75 percent.

9. The device of claim 1, wherein said application/retaining means is a contact adhesive applied to a contacting side of said film.

10. The device of claim 9, wherein said adhesive is distributed uniformly along a contacting side of said film.

11. The device of claim 9, wherein said adhesive is distributed in a continuous bond around the periphery of said film, surrounding a zone which is substantially free from said adhesive.

12. The device of claim 9, wherein said adhesive is distributed at opposing ends of said film with an intermediate zone which is substantially free from said adhesive.

13. The device of claim 1, wherein said application retaining means is a circular band.

14. The device of claim 1, wherein said application/retaining means is a mechanical applicator/holder.

15. The device of claim 1, further comprising a coating means for protecting said film from contamination.

16. The device of claim 15, wherein said coating means contains a background.

* * * * *